(12) United States Patent
Chowdhury et al.

(10) Patent No.: US 6,841,598 B2
(45) Date of Patent: Jan. 11, 2005

(54) ANTISTATIC AND ANTIDUST AGENTS, COMPOSITIONS THEREOF, AND METHODS OF MANUFACTURE

(75) Inventors: Sanjoy Kumar Chowdhury, Bangalore (IN); Prakash P. Wadgaonkar, Pune (IN); Theodorus Lambertus Hoeks, Bergen op Zoom (NL); Alex Bernard Scholten, Ann Arbor, MI (US); Suresh K. Rajaraman, Troy, NY (US); Bhimrao D. Sarwade, Pune (IN); Chilukuri Ver Avadhani, Pune (IN)

(73) Assignee: General Electric Company, Schenectady, NY (US)

( * ) Notice: Subject to any disclaimer, the term of this patent is extended or adjusted under 35 U.S.C. 154(b) by 117 days.

(21) Appl. No.: 10/064,792

(22) Filed: Aug. 16, 2002

(65) Prior Publication Data

US 2004/0034131 A1 Feb. 19, 2004

(51) Int. Cl.$^7$ .............................. C08K 5/34; C08K 5/49
(52) U.S. Cl. .............................. 524/84; 524/95; 524/99; 524/104; 524/121; 524/129; 524/158; 524/159
(58) Field of Search .............................. 524/84, 95, 99, 524/104, 121, 129, 158, 159

(56) References Cited

U.S. PATENT DOCUMENTS

| | | | |
|---|---|---|---|
| 3,141,898 A | 7/1964 | Van Dyke | 260/448.2 |
| 4,093,589 A | 6/1978 | Factor et al. | 260/45.75 B |
| 4,450,249 A | 5/1984 | Schmidt et al. | 524/132 |
| 4,943,380 A * | 7/1990 | Sugiura et al. | 252/8.7 |
| 4,973,616 A | 11/1990 | Govindan | 524/106 |
| 5,430,166 A | 7/1995 | Klein et al. | 556/428 |
| 5,449,709 A | 9/1995 | Imae et al. | 524/154 |
| 5,468,793 A | 11/1995 | Ward et al. | 524/159 |
| 5,668,202 A | 9/1997 | Hirata et al. | 524/154 |
| 6,372,829 B1 | 4/2002 | Lamanna et al. | 524/99 |

FOREIGN PATENT DOCUMENTS

| | | | |
|---|---|---|---|
| EP | 0 363 094 B1 | 8/1993 | ......... C07C/211/62 |
| EP | 0 905 183 | 9/1998 | |
| EP | 0 873 986 A1 | 10/1998 | ......... C07C/215/90 |
| EP | 0 897 950 A2 | 2/1999 | ............ C08K/5/50 |
| GB | 1 030 888 A | 5/1966 | |
| JP | Hei 4-183775 | 6/1992 | ............ C09K/3/16 |
| WO | WO 84/02798 | 7/1984 | ........... G11B/23/04 |
| WO | WO 90/05129 | 5/1990 | ......... C07C/215/40 |
| WO | WO 01/25326 A1 | 4/2001 | ............ C08K/5/00 |
| WO | WO 01/49925 A1 | 7/2001 | .......... D06M/13/46 |

OTHER PUBLICATIONS

International Search Report, International Application No. PCT/US 03/ 20101; International Filing Date Jun. 24, 2003, Date of Mailing Sep. 22, 2003, 6 pages.

English Abstract of EP 0897950 A3, published Feb. 24, 1999.

English Abstract of JP 7331231, published Dec 19, 1995.

English Abstract of EP 0 023 650 published on May 22, 1984.

English Abstract of JP 2000095970 published on Apr. 4, 2000.

S.C. Sethi, B.C. Subba Rao, S.B. Kulkarni and S.S. Katti; "Studies in the Cashewnut Shell Liquid: Part II—Anionic Surface Active Agents from Cardanol, Tetrahydrocardanol & Their Derivatives"; Indian J. Technol., vol. 1, Sep. 1963, pp. 348–355.

Raji K. Paul and CKS Pillai; "Thermal properties of processable polyaniline with novel sulfonic acid dopants"; Polymer International; 50:381–386 (2001).

P. Bajai, A.P. Gupta, and Nishma Ojha; "Antistatic and Hydrophilic Synthetic Fibers: A Critique"; J.M.S. –Rev. Macromol. Chem. Phys., C40(2 & 3), 105–138 (2000).

Raji K. Paul, C.K.S. Pillai; "Melt/solution processable conducting polyaniline with novel sulfonic acid dopants and its thermoplastic blends", Synthetic Metals 114 (2000) 27–35.

\* cited by examiner

*Primary Examiner*—Kriellion A. Sanders

(57) ABSTRACT

A quaternary onium aromatic sulfonate represented by the formula:

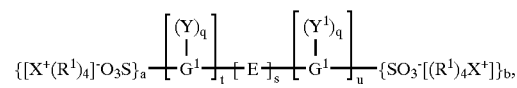

wherein each $R^1$ independently comprises substituted or unsubstituted, aliphatic or aromatic, hydrocarbyl, carbocyclic or heterocyclic radicals, each X is selected from the group consisting of phosphorus and nitrogen; wherein "a" has a value of 0, 1 or 2, and "b" has a value of 0 or 1 with the proviso that (a+b) is equal to 1 or 2; $G^1$ is an aromatic group; E comprises a bis(carbonyloxyalkyl) polydiorganosiloxane, a bis (carbonyloxyaryl) polydiorganosiloxane, and an ether linkage; each Y independently comprises hydrogen, a monovalent hydrocarbon group, alkenyl, allyl, halogen, bromine, chlorine; nitro; and OR, wherein R is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when E is an ether linkage, then X is phosphorus.

9 Claims, No Drawings

ANTISTATIC AND ANTIDUST AGENTS, COMPOSITIONS THEREOF, AND METHODS OF MANUFACTURE

BACKGROUND OF INVENTION

This disclosure generally relates to compositions comprising at least one polymer and at least one antistatic agent and more particularly, relates to fibers, films, fabrics, coatings, and molded or blown articles comprising the antistatic polymer compositions. In other aspects, this disclosure also relates to processes for imparting antistatic characteristics to substrates.

Static electricity is generated whenever dissimilar materials move or abrade against another object. In the case of immobile objects, even friction on the surface with ambient air can create static electricity. The charge capacity of a substance, defined as the capacity to generate static electricity, depends on, among others, the condition of its surface, the dielectric constant, the surface resistivity, and the relative humidity. Because charge capacity is directly proportional to the surface resistivity, it follows that a material with higher surface resistivity, or one that is better insulator will tend to generate a greater static charge. Accumulated static charge on an insulating surface can range from a few volts up to several hundred thousand volts. Thus, electrostatic discharge becomes an increasingly worrying issue at higher levels of static charge buildup. High levels of static electricity can cause permanent damage to electronic components that work typically at microvolt levels.

Most of the polymers that are used to make plastics are extremely good insulators, or in other words, they have an extremely low surface conductance, or an extremely high surface resistivity. This property makes polymers useful for fabricating electrical equipment. However, polymers can build large electrical charges that create dirt-attracting forces and naturally seek a conductive discharge path. Moreover, polymers generally have very low surface conductance, thus, the decay or discharge rate lasts a very long time, a time during which the material would retain the charge, and thus attract and retain dirt particles.

Antistatic agents constitute a unique class of polymer additives and provide a measure of safety by preventing any fire, resulting from sparking, caused by an accumulation of static electricity on the surface of an article fabricated of the polymer. They also offer aesthetic values by preventing the accumulation of surface dust on the article. For example, lenses of automotive headlamps are typically made of polymers, such as polycarbonates, which have the desirable combination of heat stability, dimensional stability, transparency, and ductility. In the past, the optics system (also sometimes called "Fresnel") necessary to properly focus the headlight beam on the road did not have a smooth profile. Consequently, the dust that accumulated on the lens surface, either during the lens molding step, or during the service life of the headlamp, was not conspicuously visible. But with the automotive industry moving towards lenses with a smoother profile, the accumulated dust becomes more easily visible, therefore leading to aesthetics issues. Thus, automotive headlamp manufacturers are looking for alternative materials that have enhanced antistatic properties without, of course, compromising on the other desirable properties the current materials already possess.

Another important area, where mitigation of static charge buildup is critical, is in conveyor belt design. For the most part nowadays, metal conveyor belts have been replaced and are made mostly of plastics and/or synthetic polymeric materials. The replacement of metal with plastic has led to several distinct advantages in conveyor belt technology, such as cleanliness (plastic parts shed fewer particles), reliability (plastic conveyor belts work for very long hours without attention), relatively lower noise (plastic parts naturally damp out clanging and resonant vibration that typically accompany metal based processes), low cost to lifetime ratio (plastic parts undergo much slower mechanical abrasion than metal-based systems), modularity and flexibility, precision due to tight tolerances in the original plastic conveyor components, and automation adaptability made possible by simple retrofit of external systems under electric control.

The advantages of the plastic conveyor belts, outlined above, have served very well in meeting the needs of modern production needs over the past two decades.

Then in the 1990's, plastics-based conveyor systems began to be used in hyper-clean environments (Class 100 or higher) essential for manufacture of advanced electronics products and systems. But as product dimensions and tolerances began to approach sub-micron levels, electrostatic discharge, a phenomenon inherent in plastic materials formulated without antistatic agents, posed difficulties to the high technology manufacturer employing plastic conveyor belt components. The buildup of surface charge also results in secondary dirt contamination, which has undesirable consequences, especially for precision, high technology electronic components. Since the conveyor belt functions through a combination of motion and friction, the belts tend to build up large amounts of electrostatic charge on their surface, thus leading to an increased possibility of electrostatic discharge. The damaging consequences of an electrostatic charge on precision electronic equipments have already been described above. It therefore becomes clear that for synthetic polymers to continue to serve the increasingly demanding requirements of the conveyor belt market, more effective plastic materials capable of effective surface charge dissipation are required.

Antistatic agents have generally been applied in one of two ways: externally and internally. Spraying the surface, or dipping the polymeric plastic material in a medium containing the antistatic agent can be used to externally apply the antistatic agents. On the other hand, internally applied antistatic agents are generally added to the polymer before processing. For this reason, internal antistatic agents have to be thermally stable and be able to migrate to the surface during processing to impart the most effective antistatic decay behavior.

There are many antistatic agents having a surface-active component (surfactant-like) within its structure. Internal antistatic agents of the anionic surfactant type are generally difficult to handle because they are inferior in compatibility and uniform dispersibility. Cationic surfactants containing quaternary nitrogen have good antistatic characteristics, but have limited utility. Non-ionic surfactants generally have inferior antistatic characteristics compared to the ionic varieties. Moreover, due to the limited thermal stability of surfactants in general, they are typically not used for processing engineering thermoplastics, such as polycarbonates. Metal salts of organic sulfonic acids have been used as antistatic agents, but they are not thermally stable, and not sufficiently compatible with resins.

It is therefore desirable to identify more effective antistatic agents as additives such that they can be incorporated into polymers without adversely affecting the physical and chemical properties of the resulting polymer compositions. The antistatic additives and compositions thereof described herein are extremely useful for producing articles with outstanding abilities to dissipate static charge buildup, and mitigate or eliminate problems due to dust attraction/ repulsion. This in turn leads to enhanced performance, safety, and aesthetic features for these articles.

SUMMARY OF INVENTION

Briefly, one embodiment of the disclosure is a quaternary onium aromatic sulfonate having the formula:

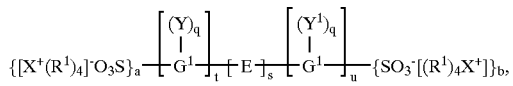

wherein each $R^1$ independently comprises aliphatic or aromatic, substituted or unsubstituted, carbocyclic or heterocyclic radicals, each X is selected from the group consisting of phosphorus and nitrogen; "a" is 0, 1 or 2, and "b" is 0, 1 or 2 with the proviso that (a+b) is an integer greater than or equal to 1; $G^1$ is an aromatic group; E comprises a bis(carbonyloxyalkyl) polydiorganosiloxane, a bis(carbonyloxyaryl) polydiorganosiloxane, and an ether linkage; each $Y^1$ independently comprises hydrogen, a monovalent hydrocarbon group, alkenyl, allyl, halogen, bromine, chlorine; nitro; and OR, wherein R is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when E is an ether linkage, then X is phosphorus.

In another embodiment, an antistatic composition comprises a melt blend of an aromatic sulfonate compound and a thermoplastic polymer, wherein the aromatic sulfonate compound is represented by the formula:

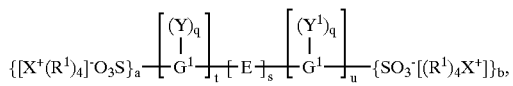

wherein each $R^1$ independently comprises aliphatic or aromatic, substituted or unsubstituted, carbocyclic or heterocyclic radicals, each "X" is selected from the group consisting of phosphorus and nitrogen; "a" is 0, 1 or 2, and "b" is 0, 1 or 2 with the proviso that (a+b) is an integer greater than or equal to 1; $G^1$ is an aromatic group; E comprises a bis(carbonyloxyalkyl) polydiorganosiloxane, a bis(carbonyloxyaryl) polydiorganosiloxane, and an ether linkage; each $Y^1$ independently comprises hydrogen, a monovalent hydrocarbon group, alkenyl, allyl, halogen, bromine, chlorine; nitro; and OR, wherein "R" is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when "E" is an ether linkage, then "X" is phosphorus.

A method of making a quaternary onium aromatic sulfonate compound comprises preparing in a solvent a first solution comprising an aromatic sulfonic acid salt having the formula:

wherein "T" is an alkali metal, "a" is 0, 1 or 2, and "b" is 0, 1 or 2 with the proviso that (a+b) is an integer greater than or equal to 1; $G^1$ is an aromatic group; "E" is an ether linkage; each $Y^1$ independently comprises hydrogen, a monovalent hydrocarbon group, halogen, and OR, wherein "R" is a monovalent hydrocarbon group; "s", "t", and "u" each represents an integer equal to one, "X" is phosphorus and "q" represents any integer from and including zero through the number of positions on $G^1$ available for substitution; contacting the first solution with an acidic medium to convert the alkali metal aromatic sulfonic acid salt to an aromatic sulfonic acid; mixing the aromatic sulfonic acid with a quaternary compound; extracting the aromatic sulfonic acid and quaternary salt mixture with an organic solvent to provide a second solution; and evaporating the organic solvent from the second solution to obtain the quaternary onium aromatic sulfonate represented by the formula:

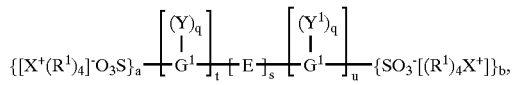

wherein each $R^1$ independently comprises aliphatic or aromatic, substituted or unsubstituted, carbocyclic or heterocyclic radicals, "a" is 0, 1 or 2, and "b" is 0, 1 or 2 with the proviso that (a+b) is an integer greater than or equal to 1; $G^1$ is an aromatic group; "E" is an ether linkage; each $Y^1$ independently comprises hydrogen, a monovalent hydrocarbon group, halogen, and OR, wherein "R" is a monovalent hydrocarbon group; "s", "t", and "u" each represents an integer equal to one, "X" is phosphorus and "q" represents any integer from and including zero through the number of positions on $G^1$ available for substitution.

In another embodiment, a method of making a quaternary onium aromatic sulfonate comprises preparing in a solvent a first solution comprising an aromatic sulfonic acid salt having the formula:

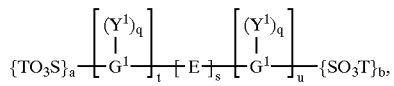

wherein "T" is an alkali metal, "a" is 1 or 2, and "b" is 0; $G^1$ is an aromatic group; each $Y^1$ independently comprises hydrogen, a monovalent hydrocarbon group, halogen, and "OR", "R" is a monovalent hydrocarbon group; "s" and "u" each represents an integer equal to zero, "q" represents any integer from and including zero through the number of positions on $G^1$ available for substitution, "t" represents an integer equal to one; contacting the first solution with an acidic medium to convert the alkali metal aromatic sulfonic acid salt to an aromatic sulfonic acid; mixing the aromatic sulfonic acid with a quaternary compound; extracting the mixture with an organic solvent to provide a second solution; and evaporating the organic solvent from the second solution to obtain the quaternary onium aromatic sulfonate represented by the formula:

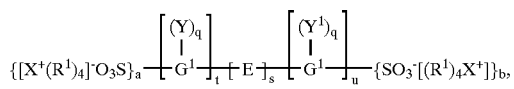

wherein each $R^1$ independently comprises aliphatic or aromatic, substituted or unsubstituted, carbocyclic or heterocyclic radicals, each "X" is selected from the group consisting of phosphorus and nitrogen; "a" is 1 or 2 and "b" is zero; $G^1$ is an aromatic group; each $Y^1$ independently comprises hydrogen, a monovalent hydrocarbon group, alkenyl, allyl, halogen, bromine, chlorine; nitro; and OR, wherein "R" is a monovalent hydrocarbon group; "t" represents an integer equal to one; "s" and "u" each represents an integer equal to zero, and "q" represents any integer from and including zero through the number of positions on $G^1$ available for substitution.

In another embodiment, a method of making a polyorganosiloxane-functionalized aromatic sulfonate comprises forming a reaction mixture comprising a hydroxyalkyl- or a hydroxyaryl-terminated polydimethylsiloxane represented by the formula:

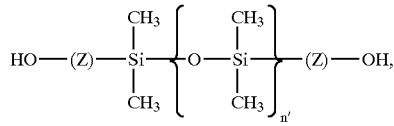

wherein "Z" is selected from the group consisting of $(CH_2)_{m'}$, wherein "m'" has a value from about 2 to about 10, and divalent substituted and unsubstituted aromatic radicals; and "n'" has a value of about 5 to about 20; a quaternary sulfonate salt of an aromatic sulfocarboxylic acid having the formula:

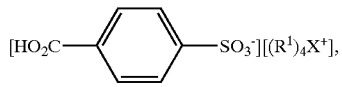

wherein each $R^1$ is independently selected from aliphatic or aromatic, substituted or unsubstituted, carbocyclic or heterocyclic radicals, and "X" is selected from the group consisting of phosphorus and nitrogen; a catalyst composition, and a solvent; stirring the reaction mixture; and heating the reaction mixture to a temperature and time effective to produce the polyorganosiloxane-functionalized aromatic sulfonate having the formula:

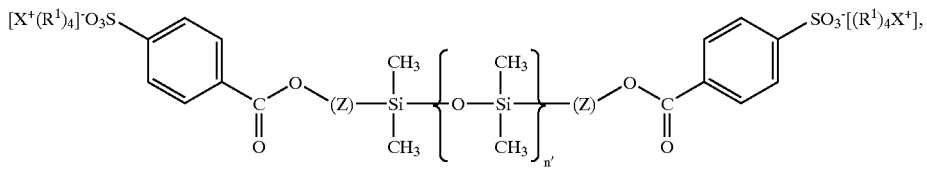

wherein each $R^1$ is independently selected from aliphatic or aromatic, substituted or unsubstituted, carbocyclic or heterocyclic radicals, and X is selected from the group consisting of phosphorus and nitrogen; "Z" is selected from the group consisting of $(CH_2)_{m'}$, wherein "m'" has a value from about 2 to about 10, and divalent substituted and unsubstituted aromatic radicals; and "n'" has a value of about 5 to about 20.

In another embodiment, a method of making a benzene-1-methoxy-3-(n-pentadecyl)-4,6-ditetrabutylphosphoniumsulfonate compound comprises contacting an aqueous solution of an alkali metal salt of a benzene-1-methoxy-3-n-pentadecyl-4,6-disulfonic acid with a strongly acidic type ion exchange resin to generate a free acid of the alkali metal salt in the aqueous solution; contacting the aqueous solution with tetra-n-butylphosphonium hydroxide in an amount effective to adjust a pH of the solution to about 5 to about 6; mixing the aqueous solution with an organic solvent; separating the organic solvent from the aqueous solution; and evaporating the organic solvent to obtain the benzene-1-methoxy-3-(n-pentadecyl)-4,6-ditetrabutylphosphoniumsulfonate compound.

A method of making an alkylated diphenyloxide tetrabutylphosphoniumsulfonate compound having the formula:

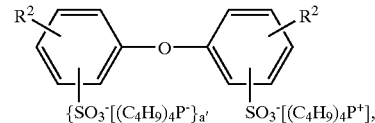

wherein "a'" has a value of about zero or one, $R^2$ can occupy an ortho or a para position on the aromatic ring, and is independently selected from the group consisting of $C_6$ to $C_{20}$ linear and branched alkyl groups; said method comprises contacting an aqueous solution with an acidic type ion exchange resin, wherein the aqueous solution comprises a compound represented by the formula:

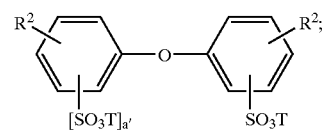

wherein "T" is selected from hydrogen and sodium, and "a'" has a value of about zero or one; contacting the aqueous solution with tetra-n-butylphosphonium hydroxide in an amount effective to adjust a pH of the aqueous solution to about 5 to about 5.5; mixing the aqueous solution with an organic solvent; separating the organic solvent from the aqueous solution; and evaporating the solvent from the solution to obtain the alkylated diphenyloxide tetrabutylphosphoniumsulfonate compound.

A method of making a bis(tetrabutylphosphonium) polyorganosiloxane-functionalized aromatic sulfonate compound having the formula:

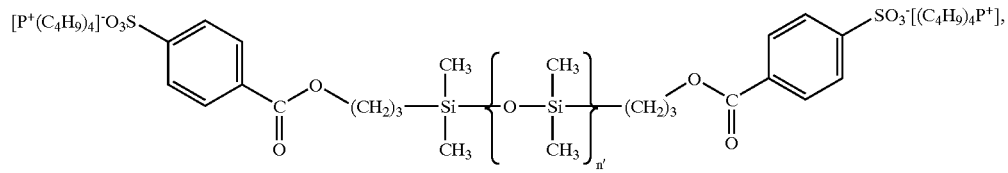

wherein "n''" is an integer having a value of about 7 comprises forming a reaction mixture comprising a hydroxyalkyl-terminated polydimethylsiloxane having the formula:

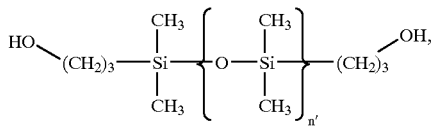

wherein "n''" is an integer with a value of about 7; a quaternary sulfonate salt of an aromatic sulfocarboxylic acid having the formula,

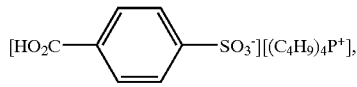

a catalyst composition comprising 1-(3-dimethylaminopropyl)-3-ethylcarbodiimide hydrochloride, 1-hydroxybenzotriazole, and triethylamine; a solvent; and heating the reaction mixture to a temperature and for a time effective to produce the bis(tetrabutylphosphonium) polyorganosiloxane-functionalized aromatic sulfonate compound.

A method of making an antistatic or antidust thermoplastic polymer molding composition comprises combining an aromatic sulfonate compound with a thermoplastic resin melt processing equipment, wherein the aromatic sulfonate compound is represented by the formula:

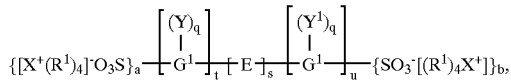

wherein each $R^1$ independently comprises aliphatic or aromatic, substituted or unsubstituted, carbocyclic or heterocyclic radicals, each X is selected from the group consisting of phosphorus and nitrogen; "a" is 0, 1 or 2, and "b" is 0, 1 or 2 with the proviso that (a+b) is an integer greater than or equal to 1; $G^1$ is an aromatic group; E comprises a bis(carbonyloxyalkyl) polydiorganosiloxane, a bis(carbonyloxyaryl) polydiorganosiloxane, and an ether linkage; each $Y^1$ independently comprises hydrogen, a monovalent hydrocarbon group, alkenyl, allyl, halogen, bromine, chlorine; nitro; and OR, wherein R is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when E is an ether linkage, then X is phosphorus.

In accordance with another embodiment, a method of making an antistatic or antidust thermoplastic polymer molding composition comprises combining an aromatic sulfonate compound with a thermoplastic resin melt processing equipment, wherein the aromatic sulfonate compound is represented by the formula:

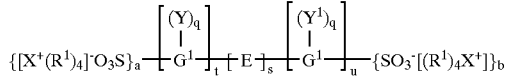

wherein each $R^1$ independently comprises aliphatic or aromatic, substituted or unsubstituted, carbocyclic or heterocyclic radicals, each X is selected from the group consisting of phosphorus and nitrogen; "a" is 0, 1 or 2, and "b" is 0, 1 or 2 with the proviso that (a+b) is an integer greater than or equal to 1; $G^1$ is an aromatic group; E comprises a bis(carbonyloxyalkyl) polydiorganosiloxane, a bis(carbonyloxyaryl) polydiorganosiloxane, and an ether linkage; each $Y^1$ independently comprises hydrogen, a monovalent hydrocarbon group, alkenyl, allyl, halogen, bromine, chlorine; nitro; and OR, wherein R is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when E is an ether linkage, then X is phosphorus.

The embodiments of the present disclosure have many advantages, including the ability to produce the antistatic compounds described above, polymer molding compositions containing these compounds, and fabrication of antistatic articles useful in automotive, electronics, conveyor belt systems, and display devices applications.

DETAILED DESCRIPTION

Disclosed herein are antistatic agents, compositions thereof, and methods of manufacture. Preferably, the antistatic agents are quaternary onium aromatic sulfonate salts represented by formula (I):

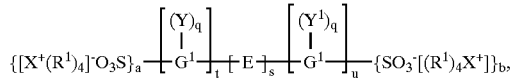

wherein each $R^1$ independently preferably comprises substituted and unsubstituted, aliphatic, aromatic, hydrocarbyl, carbocyclic, or heterocyclic radicals; each "X" is selected from the group consisting of phosphorus and nitrogen; "a" is 0, 1 or 2, and "b" is 0, 1 or 2 with the proviso that (a+b) is an integer greater than or equal to 1; $G^1$ is an aromatic group; "E" comprises a bis(carbonyloxyalkyl) polydiorganosiloxane, a bis(carbonyloxyaryl) polydiorganosiloxane, and an ether linkage; each $Y^1$ independently comprises hydrogen, a monovalent hydrocarbon group, alkenyl, allyl, halogen, bromine, chlorine; nitro; and OR, wherein "R" is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when "E" is an ether linkage, then "X" is phosphorus.

In one embodiment, "E" represents a polydiorganosiloxane of the formula (II):

wherein "$n_1$" has a value from about 5 to about 20; and $R^3$ is independently selected from $C_1$–$C_6$ linear and branched alkyl groups. In a preferred embodiment, $R^3$ is a methyl group.

The $R^1$ groups in the quaternary onium aromatic sulfonate compounds shown in formula (I) can assume a wide variation in their structures. Each $R^1$ can be the same or various combinations of the aliphatic, aromatic, hydrocarbyl, carbocyclic, and heterocyclic radicals. Suitable examples of R include, but are not limited to, $C_1$–$C_{18}$ linear and branched alkyl radicals, aralkyl, and cycloalkyl radicals. In an embodiment, $R^1$ is one selected from the group consisting of methyl, ethyl, n-propyl, n-butyl, n-pentyl, n-hexyl, n-octyl, n-dodecyl, n-hexadecyl, and n-octadecyl. In a particular embodiment, $R^1$ is an n-butyl radical.

In other embodiments, suitable $R^1$ radicals include, but are not limited to, $C_6$–$C_{14}$ aromatic substituted and unsubstituted aromatic radicals. In one embodiment, $R^1$ is preferably an unsubstituted aromatic radical selected from the group consisting of phenyl, indenyl, biphenyl, 1-naphthyl, 2-naphthyl, anthracenyl, and fluorenyl. In another embodiment, $R^1$ is preferably a $C_6$–$C_{14}$ substituted aromatic radical, which may or may not contain other heteroatom substituents. Examples of these include, but are not limited to halophenyl, chlorophenyl, dichlorophenyl, trichlorophenyl, polyhalophenyl, bromophenyl, fluorophenyl, difluorophenyl, alkoxyphenyl, alkoxycarbonylphenyl, nitrophenyl, cyanophenyl, alkylphenyl, polyalkylphenyl, tolyl, xylyl, benzyl, isopropylphenyl, isobutylphenyl, chloronaphthyl, methyinaphthyl, isopropyinaphthyl, and the like. $R^1$ substituents may also comprise mixtures of alkyl, cycloalkyl, aralkyl, and aromatic groups.

Suitable examples of the $[(R^1)_4X^+]$ fragment of the quaternary onium aromatic sulfonate compound include, but are not limited to, tetramethylammonium, tetramethylphosphonium, tetraethylammonium, tetraethylphosphonium, tetra-n-butylammonium, tetra-n-butylphosphonium, tetra-n-pentylammonium, tetra-n-pentylphosphonium, tetra-n-hexylammonium, tetra-n-hexylphosphonium, tetra-n-heptylammonium, tetra-n-heptylphosphonium, tetra-n-octylammonium, tetra-n-octylphosphonium, tetraphenylammonium, tetraphenylphosphonium, methyltriphenylammonium, methyltriphenylphosphonium, benzyltriphenylammonium, benzyltriphenylphosphonium, benzyltrimethylammonium, benzyltrimethylphosphonium, benzyltriethylammonium, benzyltriethylphosphonium, (n-hexadecyl)(tri-n-butyl) ammonium, (n-hexadecyl)(tri-n-butyl)phosphonium, (n-octadecyl)trimethylammonium, (n-octadecyl) trimethylphosphonium, (n-hexadecyl) trimethylammonium, (n-hexadecyl)trimethylphosphonium, methyl(tri-n-octyl) ammonium, methyl(tri-n-octyl)phosphonium, methyl(tri-n-decyl)ammonium, methyl (tri-n-decyl)phosphonium, (tri-n-butyl)(n-tetradecyl)ammonium, (tri-n-butyl)(n-tetradecyl) phosphonium, ethyl(tri-n-butyl)ammonium, and ethyl(tri-n-butyl) phosphonium, and the like.

The $R^1$ groups preferably do not hinder formation of the quaternary onium aromatic sulfonate compound. In one embodiment, the $R^1$ groups generally comprise 1 to 18 carbons that may further include heteroatoms such as an oxygen atom, nitrogen atom, sulfur atoms, or the like. Examples of organic groups containing oxygen atoms are hydrocarbon groups substituted with hydroxyl or alkoxy group. In other embodiments, the heteroatom containing group includes, but is not limited to, hydroxyalkyl groups such as hydroxymethyl, hydroxyethyl, hydroxypropyl, hydroxybutyl, hydroxypentyl, hydroxyhexyl, hydroxyheptyl, and hydroxyoctyl; and alkoxyalkyl groups such as methoxymethyl, ethoxymethyl, ethoxyethyl, n-propoxymethyl, isopropoxymethyl, n-butoxymethyl, n-butoxyethyl, iso-butoxyethyl, polyalkylene glycol, and the like, including mixtures thereof.

Suitable examples of heterocyclic groups for the $R^1$ group include, but are not limited to, substituted and unsubstituted pyridinium, pyridazinium, pyrimidinium, imidazolium, pyrazolium, pyrazinium, thiazolium, and oxazolium radicals. The substituted heterocyclic radicals may optionally have substituents selected from the group consisting of halogens (such as fluorine and/or chlorine), monovalent $C_1$–$C_6$ linear and branched alkyl, monovalent $C_1$–$C_6$ linear and branched alkoxy, and monovalent $C_6$–$C_{12}$ aryloxy radicals, and mixtures thereof.

In other embodiments, suitable $R^1$ groups are those obtained by different combinations of the aliphatic, aromatic, and the heteroatom containing groups described hereinabove. Other examples for the $[(R^1)_4X^+]$ moiety obtained by other combinations of different types of $R^1$ groups in different ways, as alluded to above, will be apparent to those skilled in the art.

In another particular embodiment, the quaternary onium aromatic sulfonate preferably has a structure in which each $R^1$ is an n-butyl radical, X is nitrogen, "a" is 1 or 2 and "b" is zero; "s" and "u" each represents an integer equal to zero, "t" represents an integer equal to one; $G^1$ is a tetravalent phenyl radical, and "q" represents an integer equal to two such that $Y^1$ is a methoxy and an n-pentadecyl group.

In another particular embodiment, the quaternary onium aromatic sulfonate preferably has a structure in which each $R^1$ is an n-butyl radical, X is phosphorus, "a" is 1 or 2 and "b" is zero; "s" and "u" each represents an integer equal to zero, "t" represents an integer equal to one; $G^1$ is a tetravalent phenyl radical, and "q" represents an integer equal to two such that $Y^1$ is a methoxy and an n-pentadecyl group.

In another embodiment, the quaternary onium aromatic sulfonate has a structure in which each $R^1$ is an n-butyl radical, "a" and "b" each is 1, X is phosphorus, "s", "t" and "u" each represents an integer each being equal to one; $G^1$ is a divalent aromatic radical, "q" represents an integer equal to zero, and "E" is a bis(carbonyloxyalkyl) polydiorganosiloxane linkage of the formula (III):

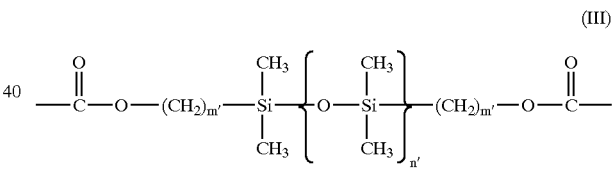

(III)

wherein "m" has a value in the range from about 3 to about 6, and "n'" has a value in the range from about 5 to about 20.

In other embodiments, the quaternary onium aromatic sulfonate has the structure in which each $R^1$ is an n-butyl radical, "a" and "b" each is 1, X is nitrogen, "s" represents an integer equal to one, "t" and "u" represent integers each being equal to one, $G^1$ is a divalent aromatic radical, "q" represents an integer equal to zero, and "E" is the bis (carbonyloxyalkyl)polydiorganosiloxane linkage of formula (III).

In yet another embodiment, the quaternary onium aromatic sulfonate preferably has a structure in which each $R^1$ is an n-butyl radical, "E" is an ether linkage, "X" is phosphorus, "a" is 0 or 1 and "b" is one with the proviso that (a+b) is 1 or 2; $R^1$ is an n-butyl radical, "s", "t", and "u" each represents an integer equal to one; $G^1$ is a tri- or tetra-substituted phenyl radical, "q" represents an integer equal to one such that $Y^1$ is an alkyl group selected from the group consisting of $C_1$ to $C_{20}$ linear and branched alkyl groups.

The quaternary onium aromatic sulfonates described hereinabove have antistatic characteristics that make them valuable as additives for preparing antistatic polymer compositions. In several embodiments of the disclosure, the term "antistatic" is also meant to include the term "antidust" since an antistatic additive, a polymer composition or an article comprising the antistatic additive would also show the ability to repel surface dust. Both thermoset and thermoplastic polymers can be used for making polymer compositions comprising the quaternary onium aromatic sulfonate. The thermoplastic polymer is preferably selected from the group consisting of condensation and addition polymers. In one embodiment, the thermoplastic polymer is an aromatic polycarbonate, a polyestercarbonate, a polyphenylene sulfide, a polyetherimide, a polyester, a polyphenylene ether, a polyphenylene ether/styrene polymer blends, a polyamide, a polyketone, acrylonitrile-butadiene-styrene copolymer, a styrene-acrylonitrile copolymer, a polyolefin, blends thereof, and blends thereof with other materials. Suitable other materials include, but are not intended to be limited to, antioxidants, thermal stabilizers, ultraviolet stabilizers, processing agents, mold release agents, fillers, flame retardants, and like additives. The polycarbonates and polyestercarbonates are preferably obtained from polymerization processes that include melt transesterification method, interfacial polymerization method, solid-state polymerization, solution, or redistribution processes, or combinations thereof.

In a particular embodiment, a thermoplastic polymer composition comprises an antistatic additive selected from the group of quaternary onium aromatic sulfonates as shown in formulas (IV), (V), and (VI). The substituent "$R^2$" (formula V) preferably occupies an ortho or a para position on the aromatic ring, and is independently selected from the group consisting of $C_1$ to $C_{20}$ linear and branched alkyl groups. The term "a'" (formula IV) preferably has a value of about zero or one. The term "n''" (formula VI) has a value of about 7.

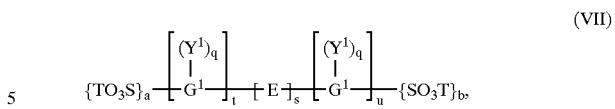

wherein "a", "b", "t", "s", "u" $G^1$, $Y^1$, and "q" are the same described earlier for formula (I); "T" is an alkali metal selected from the group consisting of lithium, sodium, potassium, rubidium, and cesium.

In various embodiments, an acidic medium is used to generate the corresponding sulfonic acid. Examples of suitable acidic mediums include strong acids such as for example sulfuric acid, fluoroalkylsulfonic acids and perfluoroalkylsulfonic acids. In a particular embodiment, the acidic medium comprises a polymeric, strongly acidic ion exchange resin bearing sulfonic acid groups. Suitable examples of polymeric, strongly acidic ion exchange resin bearing sulfonic acid groups include, but are not limited to fluorinated polymeric sulfonic acid resins, such as the Nafion® series of resins (available commercially from E. I. Dupont de Nemours), and sulfonated styrene-divinylbenzene copolymers prepared using from about 0.5 mole percent to about 20 mole percent of divinylbenzene per hundred moles of styrene employed. In particular embodiments, the sulfonated styrene-divinylbenzene copolymers comprise gelular and macroreticular varieties, corresponding to the sulfonated, low and high divinylbenzene-crosslinked styrene copolymers, respectively. An example of a gelular resin is Amberlyst-121 (sulfonated, 4% divinylbenzene-crosslinked polystyrene resin) available commercially from the Rohm and Haas Company. An example of a macroreticular resin is

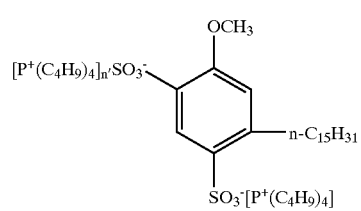

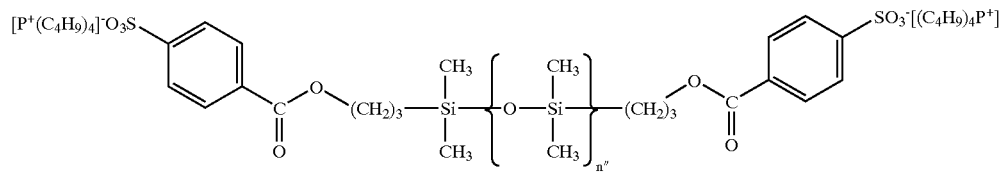

Depending upon the type of application and the type of thermoplastic polymer, the amount of the antistatic additive to be employed can vary. The thermoplastic polymer compositions preferably comprise the additive at about $2.5\times10^{-3}$ parts to about 6 parts per 100 parts of the total amount of polymer in the composition, with about $3\times10^{-2}$ parts to about 6 parts per 100 parts more preferred, and with about 0.5 parts to about 6 parts per 100 parts even more preferred.

In some embodiments, a method for preparing the quaternary onium aromatic sulfonate salts of formula (I) comprises the use of aromatic sulfonic acid salts generally represented by formula (VII):

Amberlyst-15 (sulfonated, 20% divinylbenzene-crosslinked polystyrene resin), also available commercially from the Rohm and Haas Company.

Generally, an excess of the acidic medium is preferably employed to ensure complete conversion to the sulfonic acid. In one embodiment, the acidic medium employed is a sulfonated styrene-divinylbenzene resin, and is used in an amount from about 15 times to about 20 times the number of moles of the alkali metal sulfonic acid salt. Higher amounts of the acidic medium can also be employed, but they are generally not required.

In one embodiment, the process of contacting the polymeric, strongly acidic resin with the alkali metal salt of the aromatic sulfonic acid is accomplished by allowing the solution to pass through a column packed with polymeric acidic resin. In another embodiment, contacting is effected by pumping the solution from the bottom of the packed bed column and the solution of the product mixture is collected from the top of the bed. Suitable solvents for preparing a solution comprising the alkali metal salt of the aromatic sulfonic acid comprise water, $C_1$–$C_4$ aliphatic alcohols, tetrahydrofuran, acetonitrile, $C_7$–$C_9$ aromatic hydrocarbons, and mixtures thereof. Generally the presence of water facilitates the alkali metal ion-hydrogen ion exchange process.

The aromatic sulfonic acid composition obtained from the alkali metal salt complex of formula (VII) is neutralized by contacting it with a quaternary compound represented by formula (VIII) as shown:

$$X(R^4)_4\text{—}Y \quad (VIII),$$

wherein "X" is selected from the group consisting of nitrogen and phosphorus; each $R^4$ is independently selected from substituted or unsubstituted aliphatic or aromatic radicals, or substituted or unsubstituted carbocyclic or heterocyclic radicals as previously described for the corresponding quaternary onium sulfonic acid salt of formula (I); and Y comprises a hydroxide, $OCOR^5$, or $OR^5$, wherein $R^5$ comprises a substituted or unsubstituted aliphatic, carbocyclic or aromatic, radical. In one embodiment, suitable $R^5$ groups are selected from the group consisting of $C_1$–$C_8$ linear and branched alkyl groups. In another embodiment, suitable $R^5$ groups are selected from the group consisting of $C_6$–$C_{12}$ aryl groups. These quaternary ammonium and phosphonium compounds of formula (VIII) react with a sulfonic acid group to generate the corresponding quaternary ammonium or phosphonium sulfonate compounds in the reaction mixture.

The quaternary compound of formula (VIII) is preferably selected from the group consisting of tetraethylphosphonium hydroxide, tetra-n-butylphosphonium hydroxide, tetra-n-butylammonium hydroxide, tetra-n-octylphosphonium hydroxide, and tetraphenylphosphonium hydroxide.

The temperature of the reaction mixture is preferably maintained in the range from about 10° C. to about 50° C. In one embodiment, the temperature of the reaction mixture is maintained in the range from about 20° C. to about 30° C. In another embodiment the reaction is carried out at an autogenous temperature. The pH of the reaction mixture is preferably adjusted to about 4 to about 6, with a pH of about 5 to about 5.5 more preferred.

Some surfactants are commercially available in the sulfonic acid forms. For example, Dowfax 3B0 Surfactant is commercially available in the acid form from Dow Chemical Company. In such cases commercially available sulfonic acids can be directly reacted with the quaternary compounds with adjustment of the pH as described above to furnish the quaternary onium aromatic sulfonate compound.

The quaternary onium aromatic sulfonate compound is then extracted from the product mixture using a suitable solvent. Suitable solvents include those that selectively dissolve the quaternary onium sulfonate compound. In some embodiments, suitable solvents comprise halogenated aliphatic and aromatic compounds, aliphatic and aromatic hydrocarbons, cyclic and acylic ethers, and mixtures thereof. In a particular embodiment, a suitable solvent for extraction is chloroform.

The solvent is then evaporated such that substantially all of the solvent is removed. In one embodiment, "substantially" means an amount which is greater than 90 weight percent (wt. %) removed, in other embodiments, greater than about 98 wt. % removed, in still other embodiments, greater than about 99 wt. % removed, based on the weight of solvent used. In still another embodiment, removal of substantially all the solvent means that no more condensate is obtained in the evaporation process.

For example, the method described above can be used for preparing benzene-1-methoxy-3-(n-pentadecyl)-4,6-ditetrabutylphosphoniumsulfonate (hereinafter sometime referred to as Formula (IX)). The method comprises mixing benzene-1-methoxy-3-(n-pentadecyl)-4,6-disulfonic acid with a tetra-n-butylphosphonium hydroxide quaternary compound. The required di-alkali metal salt of benzene-1-methoxy-3-(n-pentadecyl)-4,6-disulfonic acid can be prepared by employing a 3-step process starting from 3-pentadecylphenol. O-methylation of an alkali metal salt of 3-(n-pentadecyl)phenol with methyl iodide in a dipolar aprotic solvent, such as dimethylsulfoxide gives 3-(n-pentadecyl)anisole. This material is then sulfonated using concentrated sulfuric acid, oleum, or chlorosulfonic acid to form the disulfonic acid derivative. When chlorosulfonic acid is used, the product is a sulfonyl chloride derivative which upon hydrolysis forms the sulfonic acid. The disulfonic acid is isolated in a pure form as a di-alkali metal salt since this route helps in separating the organic impurities present in the sulfonation reaction mixture.

Another example of the utility of the method described above is for making an alkylated diphenyloxide tetrabutylphosphoniumsulfonate compound having the formula (V). The starting material for making the compound shown in formula (V) is represented by the formula (X):

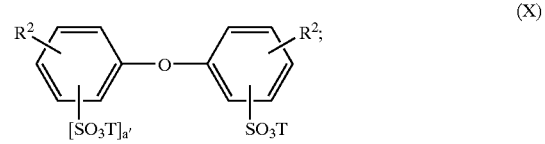

(X)

wherein "T" is selected from hydrogen and sodium, and "a'" and $R^2$ are as described previously. The sodium salts of formula (X) wherein a' is 1 is, for example commercially available from Dow Chemical Company under the trade name Dowfax® surfactants. The sulfonic acid forms of formula (X), wherein a' is 1, and $R^2$ is a $C_{10}$ or a $C_{12}$ alkyl group is, for example commercially available from Dow Chemical Company.

A polyorganosiloxane-functionalized aromatic sulfonate having the formula (VI) can be made by mixing in a suitable solvent, a hydroxyalkyl-terminated polydimethylsiloxane having the formula (XI),

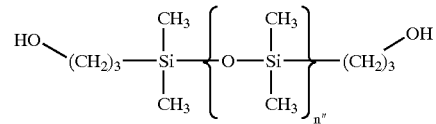

(XI), wherein "n''" has a value of about 7; a quaternary sulfonate salt of an aromatic sulfocarboxylic acid having the formula (XII):

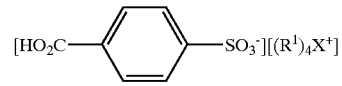

(XII), wherein $R^1$ and "X" are as previously described, and a catalyst. The resulting mixture is then preferably heated with stirring for a suitable duration to effect an esterification reaction and form the desired product. To effect complete reaction, the reaction mixture is then preferably heated to a temperature of about 50° C. to about a refluxing temperature of the reaction mixture, more preferably, to a temperature of about 70° C. to about 90° C., and even more preferably to a temperature of about 50° C. to about 70° C. The duration of heating is preferably from about 8 hours to about 30 hours, with about 12 hours to about 26 hours more preferred, and from about 18 hours to about 24 hours even more preferred.

The catalyst composition comprises at least one carbodiimide compound of the formula (XIII):

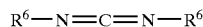

(XIII), wherein $R^6$ is independently selected from monovalent alkyl and aryl, substituted and unsubstituted radicals; 1-hydroxybenzotriazole, and at least one nitrogen base selected from the group consisting of tertiary amines of the formula $(R^7)_3N$, where $R^7$ is independently selected from $C_1$–$C_8$ linear and branched alkyl groups; and heterocyclic nitrogen bases. In one embodiment, the heterocyclic nitrogen base that can be used include, but are not limited to substituted and unsubstituted pyridines, imidazoles, and pyrrolidines. Any mixture of the foregoing list of tertiary amines and heterocyclic bases can also be used for the esterification reaction. In a particular embodiment, the carbodiimide compound is at least one selected from the group consisting of 1,3-dicyclohexylcarbodiimide, 1-[3-(dimethylamino)propyl]-3-ethylcarbodiimide hydrochloride, and 1,3-diisopropylcarbodiimide.

The solvent for the esterification reaction comprises $C_1$–$C_4$ nitriles, dichloromethane, 1,2-dichloroethane, chlorobenzene, dichlorobenzene, and chlorotoluenes. Acetonitrile is a preferred solvent for this reaction since it can be easily removed by evaporation and facilitates product isolation.

In another exemplary embodiment, the quaternary sulfonate salt of a sulfocarboxylic acid used is represented by formula (XII) in which $R^1$ is an n-butyl group, and "X" is selected from the group consisting of phosphorus and nitrogen.

In another exemplary embodiment of the method, the preparation of the bis (tetrabutylphosphonium) polyorganosiloxane-functionalized aromatic sulfonate formula (VI) as previously shown, preferably comprises the use of a solvent selected from the group consisting of $C_1$–$C_4$ nitrites, dichloromethane, 1,2-dichloroethane, chlorobenzene, dichlorobenzene, and chlorotoluenes. Acetonitrile is a preferred solvent for this reaction. Product formation is accomplished by heating the reaction mixture, whereby the temperature is maintained from about 50° C. to the refluxing temperature of the reaction mixture, and more preferably, from about 50° C. to about 85° C.

The quaternary aromatic onium sulfonate compounds may have surface migratory aptitude that can aid in dissipation of localized static charge accumulated on a polymer surface. These compounds possess a polar, hydrophilic onium sulfonate group, and a non-polar, hydrophobic moiety. While not wanting to be bound by theory, it is believed that the polar group attracts ambient moisture to form a layer of water molecules on the polymer surface. These water molecules in turn are hydrogen bonded to each other. Dissipation of the localized surface charge occurs through this hydrogen-bonded layer of water molecules, thus leading to antistatic activity.

The quaternary aromatic onium sulfonate compounds can be incorporated into polymers, particularly thermoplastic polymers, together with other additives during the molding process to afford antistatic polymer molding compositions without adversely affecting the transparency properties. Such polymer molding compositions are commercially valuable for preparing antistatic articles. In many embodiments, the articles that can be prepared using the above polymer molding compositions are those comprising forward lighting assemblies, automotive headlamp lenses, fog lamp lenses, ophthalmic devices, printer devices, and display panel devices for appliances. Examples of thermoplastic molding compositions include those comprising aromatic polycarbonate, polyestercarbonate, polyphenylene sulfide, polyetherimide, polyester, polyphenylene ether, polyphenylene ether/styrene polymer blends, polyamide, polyketone, acrylonitrile-butadiene-styrene copolymer, styrene-acrylonitrile copolymer, polyolefin, blends thereof, and blends thereof with other materials, such as glass.

Numerous approaches can be used for incorporating the quaternary aromatic onium sulfonate compounds into thermoplastic polymers. For example, a dry blending process includes preparing the polymer molding composition by mixing all of the components prior to subjecting the mixture to a molding process for fabricating the articles. The various components may include the polymer resin (powder, pellets, or the like), the quaternary aromatic onium sulfonate compounds and various additives such as, but not limited to, antioxidants, thermal stabilizers, ultraviolet stabilizers, processing agents, mold release agents, fillers, flame retardants, and the like.

Another method for incorporating the quaternary aromatic onium sulfonate compounds into thermoplastic polymers comprises combining the ingredients, including at least one and/or antidust additives discussed above, with at least one polymer in a melt processing equipment. Depending upon the nature of the antistatic additive, a solvent may be optionally added to aid in mixing with the rest of the feed mixture. In some embodiments, the processing machine may have a devolatilization system to effectively remove volatiles such as the optional solvent during the processing step. Any melt processing equipment may be employed and those skilled in the art may choose appropriate equipment without undue experimentation depending upon such factors as the type of polymer to be processed. In various embodiments suitable melt processing equipment includes, but is not limited to, extruders, kneaders, roll-mills and similar equipment. The method of molding the above molding compositions may include at least one step of injection molding, sheet molding, thermoforming, and/or blow molding.

In another embodiment, molding may be accomplished using a molten feed stream, instead of a powder and/or pellet form of the thermoplastic polymer component. This option is advantageous in a polymer production facility, wherein the final product exiting the polymerization process is in a neat molten state. Thus, the molten polymer is directly fed into a molding machine together with the quaternary aromatic onium sulfonate compound, together with other desired processing additives.

In addition to employing the compositions in molding and blow molding processes, the antistatic compositions described herein are useful for coating articles and for preparing fibers. The fibers can then be employed for manufacture of fabric and the like.

In the examples to follow, the following procedures were employed.

Glass transition temperatures (hereinafter referred to as $T_g$) were measured using a Perkin Elmer Model TGA-7 Thermogravimetric Analyzer. Percent transmission (hereinafter referred to as "% T"), yellowness index (hereinafter referred to as "YI"), and percent haze (hereinafter referred to as "% Haze") were measured using Pacific Scientific® Model XL-835 calorimeter. The percent change in melt viscosity ratio (hereinafter referred to as "% Δ MVR") was measured using a Göttfert® Rheograph 2002 instrument. Heat distortion temperature (hereinafter referred to as "HDT") is a measure of the heat deflection temperature under a load and was measured in accordance with procedure defined by ISO 75. The Vicat softening temperature (hereinafter referred to as "VICAT") is the temperature at which a plastic starts to soften rapidly and was measured in accordance with procedure defined by ISO 306.

Tulsion T-42 MP (H$^+$), an acidic gel type ion exchange resin was purchased from Thermax Limited, India. The resin had moisture content of about 50–52% and an exchange capacity of about 1.8 milliequivalents of H$^+$ per unit volume of resin in the wet state (about 4.9 milliequivalents of H$^+$ per unit volume of resin in the dry state). The Dowfax® surfactants were procured from Dow Chemical Company.

EXAMPLE 1

In this example, benzene-1-methoxy-3-(n-pentadecyl)-4,6-ditetrabutylphosphonium sulfonate (formula (IX)) was prepared.

Into a 2-liter round-bottomed flask was placed 500 milliliters (ml) of dimethyl sulfoxide, 100 grams (g) of 3-(n-pentadecyl)phenol (0.33 mol), and 73.55 g of potassium hydroxide (1.31 mol). To this mixture, 93.5 g of methyl iodide (0.66 mol) was added drop wise with stirring at room temperature. After the addition, the reaction mixture was stirred for a further 6 hours. Then the reaction mixture was poured into deionized water (1.5 liters). The organic material was extracted by addition of diethyl ether. The diethyl ether layer was separated, washed with water, dried over anhydrous sodium sulfate, and finally evaporated to afford the crude product as a viscous fluid. This material was purified by silica gel column chromatography using petroleum ether as the eluent to furnish 3-(n-pentadecyl) anisole (104.6 g, 97% of theoretical yield) having a melting range of 27–28° C.

Into a 500 ml round-bottomed flask fitted with a magnetic stirring bar and a dropping funnel was added 3-(n-pentadecyl)anisole (56 g, 0.18 mol). The contents of the flask were chilled in a cooling bath. Concentrated sulfuric acid (46.5 g, 0.48 mol) was added drop wise over a period of about 30 minutes with stirring so as to maintain an internal temperature of about 10° C. After all the sulfuric acid had been added, the cooling bath was removed, and the reaction mixture was heated to maintain a temperature of about 70° C. for about 6 hours. Then the mixture was cooled to room temperature and poured into ice-cold deionized water (500 ml) with stirring. The mixture was extracted with ethyl acetate (3×100 ml) to remove unreacted 3-(n-pentadecyl)anisole as an ethyl acetate solution. The aqueous layer was neutralized with sodium bicarbonate and cooled to about 10° C. for about 3 hours. The precipitated sodium sulfate was filtered off, and the filtrate was diluted with n-butanol (500 ml). The n-butanol solution was concentrated on a rotary evaporator under reduced pressure. Methanol (500 ml) was added to the residual material whereupon some more sodium sulfate precipitated out which was removed by filtration. The process of adding methanol, concentration under reduced pressure, subsequent addition of more methanol, and filtration was done two more times to ensure complete removal of sodium sulfate. The filtrate resulting finally was evaporated under reduced pressure to furnish crude disodium salt of benzene-1-methoxy-3-(n-pentadecyl)-4,6-disulfonic acid. This material was washed with hot ethanol (3×300 ml) to remove colored impurities.

The clarified disodium salt from above was dissolved in deionized water and the solution was passed through a column packed with Tulsion H$^+$ ion exchange resin (previously purified by washing with hot distilled water). The eluate from the column was collected and treated with tetra-n-butylphosphonium hydroxide (used as a 40% aqueous solution) until the pH of the reaction mixture was about 5.6. The reaction mixture was extracted with chloroform (500 ml); the chloroform solution was washed with deionized water, and dried over anhydrous sodium sulfate. Removal of the chloroform on a rotary evaporator, followed by drying under high vacuum using an oil pump afforded the product as a pale yellow viscous liquid. Proton NMR spectrum of the material showed that it was the desired product.

EXAMPLE 2

In this example, alkylated diphenyloxide tetrabutylphosphoniumsulfonates of formula (XIV) with R$^2$ groups having varying alkyl chain lengths (A, B, C, and D) were prepared.

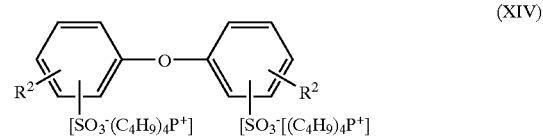

(XIV)

The alkylated diphenyloxide sulfonic acids that were commercially available were reacted with tetra-n-butylphosphonium hydroxide as follows.

A solution of tetra-n-butylphosphonium hydroxide (40% aqueous solution) was added drop wise to the appropriate alkylated diphenyloxide sulfonic acid (50 g), dissolved in about 200 ml of deionized water, with stirring at room temperature until the pH of the reaction mixture indicated a value of about 5.5. The reactions were monitored using a pH meter. The reaction mixture was extracted with dichloromethane (250 ml), and the dichloromethane layer was separated, washed three times with water, dried over anhydrous sodium sulfate, and evaporated to furnish the desired product. The data is shown in Table 1.

In those cases where the sodium salts of the alkylated diphenyloxide sulfonic acids were available, they were first converted to the corresponding sulfonic acid derivatives by treatment with an acidic ion exchange resin, such as Tulsion H$^+$ ion exchange resin, using the same procedure as described above for making the compound having formula (IX).

In this manner, the alkylated diphenyloxide sulfonate compounds (XIV-A), (XIV-B), (XIV-C), and (XIV-D) were prepared by starting from the corresponding C$_6$, C$_{10}$, C$_{12}$, and C$_{16}$ alkylated diphenyl oxide sodium sulfonic acids, respectively.

TABLE 1

| Alkyl group in the starting alkylated diphenyloxide sulfonic acids | Molecular weight | Moles of SO₃H present in 50 g of acid | Weight of TBPH (40% solution) used |
|---|---|---|---|
| $C_6$ | 430 | 0.23 | 151 |
| $C_{10}$ | 498 | 0.20 | 139 |
| $C_{12}$ | 524 | 0.19 | 132 |
| $C_{16}$ | 596 | 0.17 | 116 |

EXAMPLE 3

This example describes the synthesis of a bis (tetrabutylphosphonium) polyorganosiloxane-functionalized aromatic sulfonate compound (formula VI).

In a 1-liter beaker was placed 4-sulfobenzoic acid (20.2 g, 0.1 mol), and added deionized water (200 ml) to dissolve the material. To this solution was added 40% aqueous solution of tetra-n-butylphosphonium hydroxide (69 g, 0.1 mol). The solid that precipitated out was isolated by filtration using a sintered funnel, and washed several times with deionized water. The salt was then crystallized from tetrahydrofuran to give pure 4-(tetra-n-butylphosphoniumsulfonato)benzoic acid (m.p. 182° C.–184° C.; 32.20 g, 70% of theoretical yield). Proton NMR spectrum of the material verified the purity of the above intermediate product.

Into a 500 ml three-necked round bottom flask fitted with a magnetic stirring bar, a dropping funnel and a reflux condenser were taken allyl alcohol (117 g, 2.01 mol) and chlorotrimethylsilane (1 ml). To this mixture maintained at ambient temperature was added 1,1,1,3,3,3-hexamethyldisilazane (160.0 g, 0.99 mol) drop wise with magnetic stirring. After completion of the addition, the reaction mixture was heated under reflux for about 6 hours. Fractional distillation of the mixture furnished 227 g (88% of theoretical yield) of the intermediate product, allyloxytrimethylsilane having a boiling range from about 100° C. to about 101° C.

Into a 500 ml three-necked round bottom flask equipped with a magnetic stirring bar, a reflux condenser, and a dropping funnel was placed hydride-terminated polydimethyl siloxane (purchased from Aldrich; number average molecular weight ($M_n$)=580; 158.0 g, 0.27 mol) and 8 wt % solution of hydrogen hexachloroplatinate (1.5 ml). The mixture was heated to 60° C. and allyloxytrimethylsilane (77 g, 0.59 mol) was added drop wise over a period of about 1.5 hours. After the addition, the contents of the reaction flask was slowly heated to about 120° C. and held at that temperature for about 3 hours. Excess allyloxytrimethylsilane was then removed by distillation. The reaction mixture was cooled to room temperature and suction filtered through a Celite-magnesium sulfate-Celite bed to furnish 176.0 g, (77.20% of theoretical yield) of bis (trimethylsilyloxypropyl)-terminated poly (dimethylsiloxane) as a viscous oily product.

Into a 500 ml round bottom flask fitted with a magnetic stirring bar was taken bis (trimethylsilyloxypropyl)-terminated poly (dimethylsiloxane) prepared above (170.0 g) and 300 ml of a solution of hydrochloric acid (prepared by diluting 85 ml of 35% hydrochloric acid with 215 ml of tetrahydrofuran). The resulting mixture was stirred at room temperature for about 6 h and then diluted with diethyl ether (1000 ml). The ether solution was washed with aqueous sodium bicarbonate solution (4×200 ml), followed by washing with brine (2×200 ml). The ether solution was separated, dried over anhydrous sodium sulfate, filtered, and concentrated on a rotary evaporator. The residual oily product was distilled under reduced pressure. The fraction having a boiling range from about 65° C. to about 80° C. at about 0.06 mm Hg was collected. In this manner, 96 g of the desired bis(hydroxypropyl)-terminated poly (dimethylsiloxane) product was obtained. NMR analysis of the product indicated the material had a number average molecular weight ($M_n$) of about 770.

Into a 100 ml round bottom flask fitted with a magnetic stirring bar was placed the 4-(tetra-n-butylphosphoniumsulfonato)benzoic acid prepared as described above (1.0 g, 2.2 mmol), bis(hydroxypropyl)-terminated poly(dimethylsiloxane) (0.77 g, 1 mmol), 1-[3-(dimethylamino)propyl]-3-ethylcarbodiimide hydrochloride (0.77 g, 4 mmol), triethylamine (0.51 g, 5 mmol), 1-hydroxybenzotriazole (0.68 g, 5 mmol), and acetonitrile (20 ml). The resulting mixture was heated under reflux for about 24 h. After cooling the reaction mixture to room temperature, acetonitrile was removed under reduced pressure, and the residual material was dissolved in dichloromethane. The dichloromethane solution was successively washed with aqueous sodium bicarbonate solution, brine, water, dried over anhydrous sodium sulfate, filtered, and concentrated on a rotary evaporator to furnish the crude product as a viscous oily material. This material was purified using silica gel column chromatography. Initially, ethyl acetate was used as the eluent to remove any unreacted bis(hydroxypropyl)-terminated poly(dimethylsiloxane). Then methanol was used as the eluent to isolate the desired product bis(tetrabutylphosphonium) polyorganosiloxane-functionalized aromatic sulfonate (VI) (1.42 g, 75% of theoretical yield). Proton NMR spectrum of the material indicated that pure product had been isolated.

EXAMPLE 4

In this example, an aromatic polycarbonate resin was melt-blended with the appropriate amount of the anti-static agent as indicated below. The aromatic polycarbonate resin used in the examples was a BPA homopolycarbonate resin having an intrinsic viscosity of about 0.46 deciliters per gram as measured in dichloromethane at 20° C. The molding mixture also contained 2.7 grams of silicone oil mold release agent per kilogram of molding mixture and 3.9 grams of stabilizers per kilogram of molding mixture, the addition of which are not believed to affect the antistatic properties. The molding mixture was molded in a 25 mm twin-screw extruder using an operating temperature of about 285° C. After being extruded through a die orifice, the resulting strands were quenched in water and cut into pellets, which were dried at about 120° C. for about 2 hours (h). The dried pellets were injection molded using a single screw injection-molding machine to produce 10 centimeters (cm) square plaques having a thickness of about 2.5 millimeters (mm). The maximum temperature for the injection-molding barrel was about 285° C.

The plaques required for carrying out the static decay tests were obtained from the larger plaques prepared above. Each plaque used for the static decay test measured about 78 mm×58 mm×2.5 mm. Prior to the test, the plaques were conditioned at a temperature of about 23° C. and a relative humidity of about 50% for about three days. The static decay tests were carried out on these plaques using a Static Honestmeter, Model S-5109 instrument manufactured by Shishido Electrostatic Ltd. The applied voltage was cut-off when the surface charge attained a fixed value of about 3 kilovolts. Subsequently, the decay of surface charge was followed with time with a detector. The static half decay time (indicated by "$T_{1/2}$") represents the time at which the surface charge reached a value that was half the initial value. The above procedure was repeated for a control experiment where no antistatic additive was added. Table 2 refers to measurements made with plaques containing 25.6 mmol of the antistatic additive per kilogram of the polycarbonate. Table 3 refers to measurements made with plaques containing 1.5 weight percent of the antistatic additive relative to weight of the polycarbonate taken. "NA" in the tables means "not available".

TABLE 2

| Formula of Antistatic compound | $T_{1/2}$ (sec) | % T | YI | % Haze | ΔMVR (%) | HDT | VICAT |
|---|---|---|---|---|---|---|---|
| (IX) | 16.6 | 88.6 | 6.23 | 4.76 | 33.1 | 117.4 | 137.7 |
| (XIV-D) | 114.7 | NA | NA | NA | 36.3 | 123.1 | 141.4 |
| (VI) | 9.0 | NA | NA | NA | 155.05 | 112.5 | 131.4 |
| None* | >>1500 | 90 | NA | NA | NA | 150 | |

*Control

TABLE 3

| Formula of Antistatic compound | $T_{1/2}$ (sec) | % T | YI | % Haze | ΔMVR (%) | Tg (° C.) |
|---|---|---|---|---|---|---|
| (XIV-A) | 200 | NA | NA | NA | 87.8 | 145.4 |
| (XIV-B) | 200 | 79.0 | 12 | 77.8 | 103.4 | 145.2 |
| (XIV-C) | 127.0 | NA | NA | NA | 133.4 | 144.4 |
| None* | >>1500 | 90 | NA | NA | NA | 150 |

*Control

The results in Table 2 and Table 3 show that the antistatic compounds represented exhibit significant reduction in static decay properties compared to the control without an antistatic compound. In addition to the reduction in static decay, the polymer compositions comprising the aforementioned antistatic compounds maintain the polymers inherent physical properties, such as, for example, glass transition temperature.

While the disclosure has been illustrated and described in typical embodiments, it is not intended to be limited to the details shown, since various modifications and substitutions can be made without departing in any way from the spirit of the present invention. As such, further modifications and equivalents of the disclosure herein disclosed may occur to persons skilled in the art using no more than routine experimentation, and all such modifications and equivalents are believed to be within the spirit and scope of the disclosure as defined by the following claims. All Patents cited herein are incorporated herein by reference.

What is claimed is:

1. An antistatic or antidust composition comprising a melt blend of:
an aromatic sulfonate compound and a thermoplastic polymer, wherein the aromatic sulfonate compound is represented by the formula:

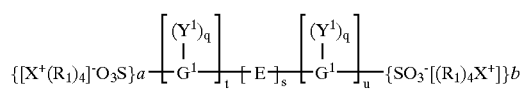

wherein each $R^1$ independently comprises aliphatic or aromatic, substituted or unsubstituted, carbocyclic or heterocyclic radicals, each X is selected from the group consisting of phosphorus and nitrogen; wherein "a" is 0, 1 or 2, and "b" is 0, 1 or 2 with the proviso that (a+b) is an integer greater than or equal to 1; $G^1$ is an aromatic group; E comprises a bis(carbonyloxyalkyl) polydiorganosiloxane, a bis(carbonyloxyaryl) polydiorganosiloxane, and an ether linkage or an ether linkage; each $Y^1$ independently comprises hydrogen, a monovalent hydrocarbon group, alkenyl, allyl, halogen, nitro; and OR, wherein R is a monovalent hydrocarbon group; "q" represents any integer from and including zero through the number of positions on $G^1$ available for substitution; "t" represents an integer equal to at least one; "s" represents an integer equal to either zero or one; and "u" represents any integer including zero; with the proviso that when E is an ether linkage, then X is phosphorus.

2. The composition of claim 1, wherein said aromatic sulfonate compound is about $2.5 \times 10^{-3}$ parts to about 6 parts per 100 parts of the thermoplastic polymer.

3. The composition of claim 1, wherein said thermoplastic polymer comprises a polycarbonate, polyestercarbonate, polyphenylene sulfide, polyetherimide, polyester, polyphenylene ether, polyphenylene ether/styrene polymer blends, polyamide, polyketone, acrylonitrile-butadiene-styrene copolymer, styrene-acrylonitrile copolymer, polyolefin, blends thereof, and blends thereof with other materials.

4. The composition of claim 1, wherein the aromatic sulfonate compound is selected from the group of formulas consisting of:

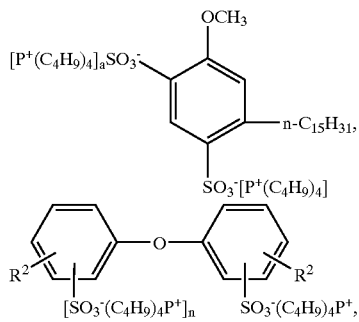

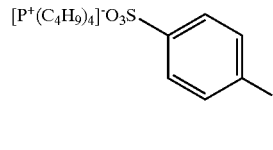

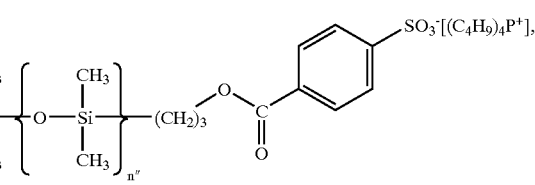

wherein "a" has a value of about zero or one, $R^2$ can occupy an ortho or a para position on the aromatic ring, and is independently selected from the group consisting of $C_6$ to $C_{20}$ linear and branched alkyl radicals; and wherein "n" has a value of about 7, and mixtures thereof.

5. A molded or blown article comprising the composition of claim 1.

6. A coating composition comprising the composition of claim 1.

7. A film comprising the composition of claim 1.

8. A fiber comprising the composition of claim 1.

9. A fabric comprising the fiber of claim 8.

* * * * *